United States Patent [19]

Esch et al.

[11] Patent Number: 4,956,455

[45] Date of Patent: Sep. 11, 1990

[54] BOVINE FIBROBLAST GROWTH FACTOR

[75] Inventors: Frederick S. Esch, Oceanside; Andrew Baird, San Diego, both of Calif.; Peter Bohlen, Uster, Switzerland; Denis Gospodarowicz, San Francisco; Nicholas C. Ling, San Diego, both of Calif.

[73] Assignee: The Salk Institute for Biological Studies, San Diego, Calif.

[21] Appl. No.: 747,154

[22] Filed: Jun. 20, 1985

Related U.S. Application Data

[63] Continuation-in-part of Ser. No. 586,518, Mar. 5, 1984, abandoned, which is a continuation-in-part of Ser. No. 670,160, Nov. 9, 1984, abandoned.

[51] Int. Cl.$^5$ ............................................. C07K 15/06
[52] U.S. Cl. .................................. 530/399; 530/820; 530/839; 530/827; 435/69.4
[58] Field of Search .................... 260/112.5 R, 112 R; 530/399, 820, 839, 827; 435/69.4

[56] References Cited

PUBLICATIONS

"Purification and Partial Characterization of an . . . Pituitary", Gambarini et al., *JBC* 257(16) 1982, pp. 9692–9697.
"Purification in High Yield of Brain Fibroblast Growth Factor . . . pH 9.6", *JBC* 257(20) 1982, pp. 1226–1276, Gospodarowicz et al.
"Brain Derived Fibroblast Growth Factor . . . Myelin", *PNAS* 75(10) 1978, pp. 4675–4678, Westall et al.

*Primary Examiner*—Garnette D. Draper
*Attorney, Agent, or Firm*—Fitch, Even, Tabin & Flannery

[57] ABSTRACT

Substantially pure bovine pituitary fibroblast growth factor, a 146 amino acid residue polypeptide, is produced. The amino acid residue sequence of bpFGF is disclosed as well as a DNA chain encoding the polypeptide. By appropriately inserting a synthesized DNA chain into a cloning vector and using the cloning vector to transform cells, synthetic bpFGF can be obtained from transformed cell lines, both prokaryotic and eukaryotic.

7 Claims, No Drawings

BOVINE FIBROBLAST GROWTH FACTOR

This application is a continuation-in-part of U.S. applications Ser. No. 586,518 filed Mar. 5, 1984 now abandoned and Ser. No. 670,160 filed Nov. 9, 1984 now abandoned. The present invention is directed to fibroblast growth factor (FGF) produced by synthetic methods, which will substantially enhance the availability of mammalian FGF.

BACKGROUND OF THE INVENTION

Both the brain and the pituitary gland have been known to contain mitogenic factors for cultured cells; however, until 1974, it was unclear what their relationship was with classical pituitary hormones, such as TSH, LH, FSH, GH and ACTH. In 1974, the identification in the pituitary gland of a growth factor called fibroblast growth factor (FGF) was reported which was shown to be distinct from pituitary hormones, Gospodarowicz, D. Nature, 249, 123-127 (1974). This growth factor is now known to have a MW of 16,415, is basic (a pI of 9.6), and is a potent mitogen for either normal diploid fibroblasts or established cell lines. Purification of an acidic brain FGF is described in U.S. Pat. Nos. 4,444,760 (Apr. 24, 1984). Later studies confirmed that, in addition to fibroblasts, FGF is also mitogenic for a wide variety of normal diploid mesoderm-derived and neural crest-derived cells, including granulocytes, adrenal cortical cells, chondrocytes, myoblasts, corneal and vascular endothelial cells from either bovine or human origin, vascular smooth muscle cells, and lens epithelial cells. FGF was also shown to substitute for platelet-derived growth factor in its ability to support the proliferation of fibroblasts exposed to plasma-supplemented medium. Consistent with its ability to stimulate the proliferation of bovine and vascular endothelial cells, FGF has a similar activity in vivo on capillary endothelial cells; therefore, FGF is considered an angiogenic factor.

Above-identified U.S. application, Ser. No. 586,518, the teachings of which are incorporated herein by reference, describes a purification of mammalian fibroblast growth factor (FGF) using reverse-phase high performance liquid chromatography (RP-HPLC). Above-identified U.S. application, Ser. No. 670,160, the teachings of which are incorporated herein by reference, describes a purification of mammalian FGF by heparin-Sepharose affinity chromatography.

Although the above-identified patent applications describe methods of purifying FGF from mammalian tissue, such as bovine pituitary tissue, these procedures may be difficult to scale up to large scale production.

The present invention provides pure FGF which may be produced by synthetic methods, and if so produced should substantially enhance the availability of mammalian FGF.

SUMMARY OF THE INVENTION

The present invention provides pure bovine pituitary fibroblast growth factor (bpFGF) which may be synthesized using recombinant DNA techniques or other suitable techniques. By bpFGF is meant the 146 amino acid residue polypeptide having the sequence set forth hereinafter. It appears most likely that in the native molecule none of the cysteine residues are disulfide bonded to each other but that there may be bonding of one or more of the cysteine residues to free cysteine molecules. However, evidence for there being no internal disulfide-bonding between cysteine residues is not fully conclusive and one or two pairs of cysteine residues may be internally bonded to each other, and if cysteine residues are internally bonded to each other it is not certain at this time which pair or pairs of cysteine residues are involved. In any case, the present invention provides biologically active peptides, whether non-bonded or randomly bonded. Because bpFGF is a relatively long-chain peptide, synthesis by a recombinant DNA technique is the synthetic method of choice, as opposed to standard chain elongation procedures involving stepwise addition of amino acid residues. Extraction and purification are possible but are not considered to be commercially feasible at the present time. Accordingly, a bpFGF-encoding DNA chain is obtained, e.g., by oligonucleotide synthesis, and the synthetic DNA chain is inserted into a cloning vector, appropriately placed therein so as to ensure its expression when the recombinant cloning vector is introduced into an organism or cell line. Synthetic bpFGF polypeptides which either have no internal disulfide bonds or which are randomly disulfide bonded exhibit biological activity.

Pharmaceutical compositions in accordance with invention include bpFGF, a bpFGF analog, biologically active fragments of bpFGF or analog bpFGF, or nontoxic salts thereof dispersed in a pharmaceutically acceptable liquid or solid carrier. Such pharmaceutical compositions can be used in clinical medicine, both human and veterinary, in acute or chronic administration for diagnostic or therapeutic purposes. bpFGF is further useful in in vitro cell proliferation procedures. Also considered to be within the scope of the invention are peptides- with additional segments added to either or both termini, such as those which arise from considerations of vector construction when the peptides are made using recombinant DNA techniques, providing that such terminal segments do not destroy the biological activity of the peptide.

DETAILED DESCRIPTION OF CERTAIN PREFERRED EMBODIMENTS

The invention provides the first known pure mammalian FGF, particularly bpFGF, and the production thereof by synthetic methods. The nomenclature used to define the peptides is that specified by Schroder & Lubke, "The Peptides", Academic Press (1965), wherein in accordance with conventional representation the residue having the free alpha-amino group at the N-terminus appears to left and the residue having the alpha-carboxyl group a the C-terminus to the right. Where the amino acid residue has isomeric forms, it is the L-form of the amino acid that is represented. The invention provides peptides having the formula:

```
 1    2    3    4    5    6    7    8    9   10   11   12   13   14   15
 H—Pro—Ala—Leu—Pro—Glu—Asp—Gly—Gly—Ser—Gly—Ala—Phe—Pro—Pro—Gly—

16   17   18   19   20   21   22   23   24   25   26   27   28   29   30
His—Phe—Lys—Asp—Pro—Lys—Arg—Leu—Tyr—Cys—Lys—Asn—Gly—Gly—Phe—
```

| 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|
| Phe— | Leu— | Arg— | Ile— | His— | Pro— | Asp— | Gly— | Arg— | Val— | Asp— | Gly— | Val— | Arg— | Glu— |

| 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|
| Lys— | Ser— | Asp— | Pro— | His— | Ile— | Lys— | Leu— | Gln— | Leu— | Gln— | Ala— | Glu— | Glu— | Arg— |

| 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|
| Gly— | Val— | Val— | Ser— | Ile— | Lys— | Gly— | Val— | Cys— | Ala— | Asn— | Arg— | Tyr— | Leu— | Ala— |

| 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|
| Met— | Lys— | Glu— | Asp— | Gly— | Arg— | Leu— | Leu— | Ala— | Ser— | Lys— | Cys— | Val— | Thr— | Asp— |

| 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|
| Glu— | Cys— | Phe— | Phe— | Phe— | Glu— | Arg— | Leu— | Glu— | Ser— | Asn— | Asn— | Tyr— | Asn— | Thr— |

| 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|
| Tyr— | Arg— | Ser— | Arg— | Lys— | Tyr— | Ser— | Ser— | Trp— | Tyr— | Val— | Ala— | Leu— | Lys— | Arg— |

| 121 | 122 | 123 | 124 | 125 | 126 | 127 | 128 | 129 | 130 | 131 | 132 | 133 | 134 | 135 |
|---|---|---|---|---|---|---|---|---|---|---|---|---|---|---|
| Thr— | Gly— | Gln— | Tyr— | Lys— | Leu— | Gly— | Pro— | Lys— | Thr— | Gly— | Pro— | Gly— | Gln— | Lys— |

| 136 | 137 | 138 | 139 | 140 | 141 | 142 | 143 | 144 | 145 | 146 |
|---|---|---|---|---|---|---|---|---|---|---|
| Ala— | Ile— | Leu— | Phe— | Leu— | Pro— | Met— | Ser— | Ala— | Lys— | Ser—Y | wherein Y is OH or NH$_2$. It is uncertain whether the C-terminus of the native molecule is amidated. For purposes of this application, bpFGF peptides should be considered to consituted piptides having the 146 amino-acid-residue sequence as well as biologically active fragments thereof.

From presently available evidence it is most likely that there is not internal disulfide-bonding between cysteine residues of the chain. However, two of the cysteine residues may be internally disulfide-bonded to each other, and although it appears unlikely, disulfide bonding may occur between two pairs of the cysteine residues. Also, one or more of the cysteine residues which are not involved in internal disulfide bonding may be instead bonded to free cysteine. The invention is intended to encompass synthetically produced bpFGF polypeptides in which the cysteines are free or form internal disulfide bonds randomly, i.e., between positions 25 and 69; 25 and 87; 25 and 92; 69 and 87; 69 and 92; 87 and 92; 25 and 69 plus 87 and 92; 25 and 87 plus 69 and 92; and 25 and 92 plus 69 and 87. A mixture of FGF proteins in which cysteine residues are randomly non-bonded or bonded exhibits at least some biological activity. Herein, bpFGF is also referred to as "basic FGF", having a basic pI of 9.6 (in contrast to acidic FGF which has an acidic pI of about 5).

Regardless of the effect of cysteine disulfide bonding positions on biological activity, bpFGF polypeptides produced by recombinant DNA techniques are generally biologically active. This may be because the three-dimensional structure which the bpFGF assumes within cells is the correct structure. The three-dimensional structure which the molecule assumes through natural folding and through hydrophobic and hydrophilic interactions with aqueous media may promote correct bonding or non-bonding between cysteine residues. Also, enzymatic regulatory mechanisms within cells may help to ensure correct disulfide bonding or non-bonding, either by preventing bonding or by directing disulfide bonding between particular cysteine residues. Enzymes might also cleave "incorrect" bonding to enable the molecule to reorientate itself and assume the correct natural structure. Cysteine residues that are not internally bonded may be disulfide-bonded to free cysteine moieties. It may also be that the three-dimensional structure of the molecule is such that random bonding or non-bonding of cysteine residues either with each other or to free cysteines does not substantially affect the biological structure of the protein molecule.

To synthesize a protein having the bpFGF amino acid residue sequence by recombinant DNA, a double-stranded DNA chain which encodes bpFGF is synthetically constructed. The segment of the DNA chain that encodes bpFGF is, of course, designed according to the genetic code; however, because of the degeneracy of the genetic code, a wide variety of codon combinations can be selected to form the DNA chain that encodes the product polypeptide. It is known that certain particular codons are more efficient for polypeptide expression in certain types of organisms, and the selection of codons preferably is made according to those codons which are most efficient for expression in the type of organism which is to serve as the host for the recombinant vector. However, any correct set of codons will encode product, even if slightly less efficiently. Codon selection may also depend upon vector construction considerations; for example, it may be necessary to avoid placing a restriction site in the DNA chain if, subsequent to inserting the synthetic DNA chain, the vector is to be manipulated using the restriction enzyme that cleaves at such a site. Also, it is necessary to avoid placing restriction sites in the DNA chain if the host organism which is to be transformed with the recombinant vector containing the DNA chain is known to produce a restriction enzyme that would cleave within the DNA chain.

In addition to the bpFGF-encoding sequences, the DNA chain that is synthesized may contain additional sequences, depending upon vector construction considerations. Typically, the DNA chain is synthesized with linkers at its ends to facilitate insertion into restriction sites within a cloning vector. The DNA chain may be constructed so as to encode the bpFGF amino acid sequences as a portion of a fusion polypeptide; and if so, it will generally contain terminal sequences that encode amino acid residue sequences that serve as proteolytic processing sites, whereby the bpFGF polypeptide may be proteolytically cleaved from the remainder of the fusion polypeptide. The terminal portions of the synthetic DNA chain may also contain appropriate start and stop signals.

To assemble a bpFGF-encoding DNA chain, oligonucleotides are constructed by conventional methods, such as procedures described in T. Manatis et al., *Cold Spring Harbor Laboratory Manual,* Cold Spring Harbor, New York (1982)(hereinafter, CSH). Sense and antisense oligonucleotide chains, up to about 70 nucleotide residues long, are synthesized, preferably on automated synthesizers, such as the Applied Biosystem Inc. model 380A DNA synthesizer. The oligonucleotide chains are constructed so that portions of the sense and antisense oligonucleotides overlap, associating with each other through hydrogen binding between complementary base pairs and thereby forming double stranded chains, in most cases with gaps in the strands. Subsequently, the gaps in the strands are filled in and oligonucleotides of each strand are joined end to end with nucleotide triphosphates in the presence of appropriate DNA polymerases and/or with ligases.

As an alternative to construction of a synthetic DNA chain through oligonucleotide synthesis, cDNA corresponding to bpFGF may be prepared. A cDNA library or an expression library is produced in a conventional manner by reverse transcription from messenger RNA (mRNA) from a bpFGF-producing cell line. To select clones containing bpFGF sequences, hybridization probes (preferably mixed probes to accommodate the degeneracy of the genetic code) corresponding to portions of the FGF protein are produced and used to identify clones containing such sequences. Screening of the expression library with FGF antibodies may also be used, alone or in conjunction with hybridization probing, to identify or confirm the presence of bpFGF-encoding DNA sequences in DNA library clones. Such techniques are taught, for example in CSH, supra.

The double-stranded bpFGF-encoding DNA chain is constructed or modified with insertion into a particular appropriate cloning vector in mind. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as $E.$ $Coli$, the DNA chain will be inserted 3' of a promoter sequence, a Shine-Delgarno sequence (or ribosome binding site) that is within a 5' non-translated portion and an ATG start codon. The ATG start codon is appropriately spaced from the Shine-Delgarno sequence, and the encoding sequence is placed in correct reading frame with the ATG start codon. The cloning vector also provides a 3' non-translated region and a translation termination site. For insertion into a eukaryotic cell, such as a yeast cell or a cell line obtained from a higher animal, the bpFGF-encoding oligonucleotide sequence is appropriately spaced from a capping site and in correct reading frame with an ATG start signal. The cloning vector also provides a 3' non-translated region and a translation termination site.

Prokaryotic transformation vectors, such as pBR322, pMB9, Col El, pCRl, RP4 and lambda-phage, are available for inserting a DNA chain of the length which encodes bpFGF with substantial assurance of at least some expression of the encoded polypeptide. Typically, such vectors are constructed or modified to have a unique restriction site(s) appropriately positioned relative to a promoter, such as the lac promoter. The DNA chain may be inserted with appropriate linkers into such a restriction site, with substantial assurance of production of bpFGF in a prokaryotic cell line transformed with the recombinant vector. To assure proper reading frame, linkers of various lengths may be provided at the ends of the bpFGF-encoding sequences. Alternatively, cassettes, which include sequences, such as the 5' region of the lac Z gene (including the operator, promoter, transcription start site, Shine Delgarno sequence and translation initiation signal), the regulatory region from the tryptophane gene (trp operator, promoter, ribosome binding site and translation initiator), and a fusion gene containing these two promoters called the trp-lac or commonly called the Tac promoter are available into which the synthetic DNA chain may be conveniently inserted and then the cassette inserted into a cloning vector of choice.

Similarly, eukaryotic transformation vectors, such as, the cloned bovine papilloma virus genome, the cloned genomes of the murine retroviruses, and eukaryotic cassettes, such as the pSV-2 gpt system (described by Mulligan and Berg, $Nature$ 277, 108–114, 1979) the Okayama-Berg cloning system (Mol. Cell Biol. 2, 161–170, 1982), the expression cloning vector recently described by Genetics Institute ($Science$ 228, 810–815, 1985), are available which provide substantial assurance of at least some expression of bpFGF in the transformed eukaryotic cell line.

A convenient way to ensure production of FGF or a polypeptide of a similar length is to produce the polypeptide initially as a segment of a gene-encoded fusion polypeptide. In such case, the DNA chain is constructed so that the expressed polypeptide has enzymatic processing sites flanking the bpFGF amino acid residue sequences. A bpFGF-encoding DNA chain may be inserted, for example, into the beta-galactosidase gene for insertion into $E.$ $Coli$, in which case, the expressed fusion polypeptide is subsequently cleaved with proteolytic enzymes to release the bpFGF from beta-galactosidase peptide sequences.

An advantage of inserting the bpFGF-encoding sequence so that the bpFGF sequence is expressed as a cleavable segment of a fusion polypeptide, e.g., as the bpFGF peptide sequence fused within the beta-galactosidase peptide sequence, is that the endogenous polypeptide into which the bpFGF sequence is inserted is generally rendered non-functional, thereby facilitating selection for vectors encoding the fusion peptide.

EXAMPLE 1

The structure of bpFRF was determined as follows:

Frozen bovine pituitaries were homogenized with a Waring blender for 5 minutes in 0.15 M ammonium sulfate (4 liter/kg tissue). The pH was then adjusted to 4.5 with HCl and the homogenate stirred vigorously for 2 hours. After centrifugation (18,000×g, 30 minutes) the supernatant was retained, and 230g ammonium sulfate per liter of supernatant were added; the pH was adjusted to 6–6.5 with NaOH; and the precipitation was allowed to proceed for 15 hours. After centrifugation of the reaction mixture (18,000×g, 30 min), the supernatant was retained; 300g ammonium sulfate were added to each liter of the supernatant; and then the mixture stirred well for two hours. After centrifugation of the reaction mixture (18,000×g, 30 min), the pellet was retained, and the cumulative pellets from 3 kg starting tissue was dissolved in 200 ml distilled water and dialyzed against 20 liters of distilled water overnight. The pH of the dialyzed retentate was then adjusted to 6, and the solution was clarified by centrifugation (12,000×g, 30 min). The dialyzed retentate constitutes a dialyzed extract.

Basic FGF was subsequently isolated from the dialyzed, clarified extract using three successive protocols;

two of these employed conventional ion-exchange and reverse phase HPLC purification steps as described previously (P. Bohlen et al. *Proc. Natl. Acad. Sci. USA* 81, 5364–5368 (1984)). The third method utilized heparin-Sepharose affinity chromatography in a key purification step as detailed as follows in the order in which they were performed.

(A) CM-Sephadex (C50) ion-exchange chromatography.

A 7×9 cm column of carboxymethyl Sephadex (C50) was washed with 1 liter of 50 mM sodium phosphate, 1.5 M sodium chloride, pH 6.0 and then equilibrated with 0.1 M sodium phosphate, pH 6.0. The dialyzed extract from 3 kg bovine pituitaries was loaded onto the column, and the column was washed sequentially with 0.1 M sodium phosphate, pH 6.0 containing a) no NaCl, b) 0.2 M NaCl and c) 0.65 M NaCl, allowing the $OD_{280}$ to reach a minimum value before initiating each new wash. Fractions of 18 ml were collected at 3 ml/min at 4° C. and subjected to radioimmunoassay. (B) Heparin-Sepharose chromatography.

The 0.65 M NaCl eluate from CM-Sephadex chromatography was loaded onto a 3×3 cm column of heparin-Sepharose (Pharmacia) previously equilibrated with 10 mM Tris-HCl, 0.6 M NaCl, pH 7.0 at room temperature. The column was then washed sequentially with 10 mM Tris-HCl, pH 7.0 containing a) 0.6 M NaCl and b) 1.1 M NaCl, allowing the $OD_{280}$ to reach a minimum value with each wash. The basic FGF was then eluted with a linear gradient in 10 mM Tris-HCl, pH 7.0 containing 100 ml 1.1 M NaCl and 100 ml 2 M NaCl. Fractions of 5 ml were collected at 0.8 ml/min and subjected to radioimmunoassay.

(C) Reverse phase liquid chromatography.

The basic FGF from heparin-Sepharose chromatography was pumped onto a Vydac C-4 (0.46×25 cm) reverse phase column (The Separations Group, Inc.) using a 0.1% trifluoroacetic acid (TFA)/acetonitrile solvent system (F. S. Esch et al. *Methods in Enzymol.* (ed. Conn, P.) 103, Academic Press, NY, pp. 72–89 (1983)) and eluted at 0.6 ml/min. with a 90 min. gradient of 23% to 35% acetonitrile. Fractions of 3 ml were collected at room temperature and subjected to radioimmunoassay.

In the above mentioned Radioimmunoassays (RIA) for basic FGF, antibodies were generated against a synthetic analog of the amino terminal sequence of basic FGF, [Tyr[10]]FGF(1-10), i.e. the decapeptide H-Pro-Ala-Leu-Pro-Glu-Asp-Gly-Gly-Ser-Tyr-Oh, which is conjugated to bovine serum albumin, and were subsequently used to develop the radioimmunoassay for basic FGF, as described in A. Baird et al. *Regulatory Peptides* 10, 309–317 (1985).

Because it is not possible to quantitate unmodified cysteine by amino acid analysis, cysteine residues were modified either by reduction and alkylation with [14C] iodoacetamide (New England Nuclear) or oxidization with performic acid as indicated below. In either case, the FGF in 0.1% TFA/acetonitrile was dried in a 1.5 ml polypropylene microfuge tube in a Speed Vac vacuum centrifuge (Savant, Inc.) just prior to modification.

The reduction and alkylation of cysteine residues was performed in order to radioactively label cysteine residues, making it possible to determine which fragments of subsequent cleavage reactions contain cysteine residues. The dried bpFGF was dissolved in 0.1 ml deoxygenated 0.5M Tris-HCl pH 7.7, 10mM EDTA, 6M guanidine-HCl. Dithiothreitol was added to a final concentration of 5–10 mM, and the reduction was allowed to proceed at 37° C. for 30 min. A 0.5-fold molar excess of [14C] iodoacetamide (24 mCi/mmole) over total sulfhydryl groups was added, and the incubation continued at 37° C. for 60 min. in the dark. The alkylation was terminated by addition of a large excess of dithiothreitol over iodoacetamide, and the alkylated FGF was purified by reverse phase-high performance liquid chromatography.

Performic acid oxidation of cysteine converts cysteine to cysteic acid, and the cysteic acid content of the protein is measurable by amino acid analysis. Performic acid was generated by incubating 9 ml distilled formic acid with 1 ml 30% $H_2O_2$ at room temperature in a tightly capped tube for 1 hour. 0.25 ml of this solution was employed to dissolve the dried FGF (5–15 nmoles), and the oxidation was permitted to continue at 0° C. for 2.5 hours. Four lyophilizations from distilled water were employed to remove reaction by-products.

Basic FGFs (with cysteines modified by each method described above) were proteolytically and chemically digested to obtain fragments for further analysis, including sequence analysis. Prior to any digestion, the FGF was dried in a polypropylene microfuge tube in a Speed Vac vacuum centrifuge from volatile RP-HPLC solvents.

In order to obtain multiple, overlapping FGF fragments, three types of proteolytic digestions of bpFGFs, with cysteines modified by each method described above, were performed as follows. The dried FGF (1–5 nmoles) was dissolved in 0.01 ml 0.5 M Tris-HCl pH 7.7, 10 mM EDTA, 6 M guanidine-HCl and then diluted to 1 ml with 1% $NH_4HCO_3$. Submaxillaris protease or chymotrypsin was added in a 1/50 (w/w) ratio while digestions with Staphylococcus aureus V8 employed a 1:35 (mol:mol) ratio of enzyme to substrate. Submaxillaris protease cleaves at the C-terminus of arginine; Staphylococcus aureus V8 cleaves at the C-terminus of glutamic acid; and chymotrypsin cleaves at the C-terminus of several amino acid residues having bulky aromatic or hydrophobic groups. Incubations were allowed to proceed overnight at 37° C.

Digestion with cyanogen bromide, which cleaves proteins at the C-terminus of Met, were performed on bpFGFs, with cysteines modified by each method described above, as follows. The dried, alkylated FGF (5–6 nmoles) was dissolved with 0.05 ml 70% formic acid and reduced in a solution of 2.9 M N-methylmercaptoacetamide in 7% formic acid (R. Houghten et al. *Methods in Enzymol.* (eds. Hirs., C. & Timasheff, S.) 91, Academic Press, NY, pp. 549–559 (1983)) for 24 hours at 37° C. The alkylated, reduced FGF was purified by RP-HPLC, dried in a Speed Vac vacuum centrifuge and redissolved in 0.1 ml deoxygenated 70% formic acid. A 100-fold excess of cyanogen bromide was added and the incubation continued at room temperature in the dark overnight.

Reverse phase-high performance liquid chromatography purifications of modified bpFGFs and their digestion fragments were accomplished using a Brownlee RP-300 reverse phase column (0.46×25 cm) and a 0.1% TFA/acetonitrile or a 0.1% heptafluorobutyric acid (HFBA)/acetonitrile solvent system (Esch et al. (1983) supra.).

Amino acid analyses and gas phase micro-sequencing of intact bpFGF and its digestion fragments were carried out by methods previously described (P. Bohlen et al. *Anal. Biochem.* 126, 144–152 (1982); F. S. Esch *Anal. Biochem.* 136, 39–47 (1984)). PhNCS-($^{14}$C)-carboxyamidomethylcysteine was identified during sequence analysis by liquid scintillation counting of the residues from the sequencer. The identification of cysteic acid in a given cycle was accomplished by comparison of the amino acid composition of the peptide and the remainder of its sequence as determined by Edman degradation. Carboxypeptidase Y was obtained from Pierce and utilized according to the manufacturer's recommendations. Carboxyl terminal analysis via tritium incorporation was accomplished as previously described (H. Matsuo et al. *Protein Sequence Determination* (ed., Needleman, S. B.) Springer-Verlag, NY, pp. 104–113 (1979)).

The highly efficient purification procedure, described above, permitted the rapid isolation of large quantities (about 30 to 60 nmoles per week) of highly purified basic FGF from bovine pituitaries. This source aided in the structural characterization effort. The heparin-Sepharose affinity chromatography purification step resulted in a several thousand-fold purification of two biologically active and basic FGF-immunoreactive mitogens, eluting at approximately 1.4 M and 1.95 M NaCl. A single step of RP-HPLC effected peptide homogeneity in each case. NaDodSO$_4$ PAGE yielded identical molecular weight estimates for both species, and gas phase micro-sequencing showed that both possessed identical amino terminal amino acid sequences through at least the amino-terminal 24 residues of each polypeptide. Pituitary extracts yielded approximately 15 times more of the mitogen eluting at 1.4 M NaCl than of the later eluting species, and hence, the former was selected for further structural characterization.

NaDodSO$_4$ PAGE suggested a molecular weight of 16,250±1000 for bovine pituitary basic FGF and a protein containing about 140 amino acid residues. Table I below shows the amino acid compositions obtained for the cationic mitogen from bovine brain and hypothalamus by R. R. Lobb et al., *Biochem.* 23, 6295–6299 (1984) as well as the compositional data obtained for basic FGF from bovine pituitary, all data being normalized for a 146 amino acid structure. The similarity of the compositions suggests that these structures are closely related, if not identical. In fact, basic FGF from bovine brain has been isolated, and it has been determined that its amino terminal sequence, i.e. Pro-Ala-Leu-Pro-Glu-Asp-Gly-Gly-Ser, is identical to that of the pituitary-derived molecule.

TABLE 1

Amino Acid compositions of basic FGF from different bovine tissues

| Amino Acid | Brain[a] | Hypothalamus[a] | Pituitary Basic FGF[b] | (1-146) |
|---|---|---|---|---|
| Asx | 13.7 | 13.0 | 12.4 ± 0.4 | 12 |
| Thr | 5.1 | 4.9 | 3.9 ± 0.3 | 4 |
| Ser | 10.0 | 10.0 | 9.4 ± 0.6 | 10 |
| Glx | 13.2 | 14.2 | 14.1 ± 0.4[c] | 12 |
| Pro | 11.6 | 11.3 | 9.4 ± 0.6 | 10 |
| Gly | 17.3 | 18.2 | 16.6 ± 0.6[c] | 15 |
| Ala | 9.1 | 9.0 | 9.5 ± 0.4 | 9 |
| Cys | n.d. | n.d. | 4.3 ± 0.2[d] | 4 |
| Val | 5.8 | 5.7 | 5.9 ± 0.7 | 7 |
| Met | 2.4 | 2.4 | 1.6 ± 0.4 | 2 |
| Ile | 3.2 | 3.1 | 3.4 ± 0.5 | 4 |
| Leu | 12.6 | 12.9 | 13.4 ± 0.4 | 13 |
| Tyr | 6.5 | 6.2 | 6.8 ± 0.4 | 7 |
| Phe | 7.9 | 7.6 | 7.5 ± 0.2 | 8 |
| His | 3.2 | 3.2 | 2.4 ± 0.6 | 3 |
| Lys | 13.7 | 13.5 | 13.9 ± 0.7 | 14 |
| Arg | 10.8 | 10.4 | 11.6 ± 0.3 | 11 |
| Trp | n.d. | n.d. | 0.4 ± 0.2 | 1 |

[a]Data from Lobb et al. supra. normalized for 146 amino acids.
[b]Amino acid composition of basic FGF deduced from sequence analysis.
[c]Discrepancy between amino acid and sequence analysis data greater than that expected from statistical analysis.
[d]Cysteine was determined as cysteic acid after RP-HPLC purification of performic acid oxidized basic FGF.

EXAMPLE 2

Using conventional methods, described in CSH, supra., a synthetic bpFGF gene is constructed having the following formula:

```
5' AATTCATGCCAGCCCTACCAGAAGATGGGGGGTCCGGGGCCTTCCCACCAGGG
3'     GTACGGTCGGGATGGTCTTCTACCCCCCAGGCCCCGGAAGGGTGGTCCC

CACTTCAAAGATCCAAAACGACTATATTGTAAAAACGGGGGGTTC
GTGAAGTTTCTAGGTTTTGCTGATATAACATTTTTGCCCCCCAAG

TTCCTACGAATCCACCCAGATGGGCGAGTAGATGGGGTACGAGAA
AAGGATGCTTAGGTGGGTCTACCCGCTCATCTACCCCATGCTCTT

AAATCCGATCCACACATCAAACTACAACTACAAGCCGAAGAACGA
TTTAGGCTAGGTGTGTAGTTTGATGTTGATGTTCGGCTTCTTGCT

GGGGTAGTATCCATCAAAGGGGTATGTGCCAACCGATATCTAGCC
CCCCATCATAGGTAGTTTCCCCATACACGGTTGGCTATAGATCGG

ATGAAAGAAGATGGGCGACTACTAGCCTCCAAATGTGTAACCGAT
TACTTTCTTCTACCCGCTAGTGATCGGAGGTTTACACATTGGCTA

GAATGTTTCTTCTTCGAACGACTAGAATCCAACAACTATAACACC
CTTACAAAGAAGAAGCTTGCTGATCTTAGGTTGTTGATATTGTGG

TATCGATCCCGAAAATATTCCTCCTGGTATGTAGCCCTAAAACGA
ATAGCTAGGGCTTTTATAAGGAGGACCATACATCGGGATTTTGCT

ACCGGGCAATATAAACTAGGGCCAAAAACCGGGCCAGGGCAAAAA
TGGCCCGTTATATTTGATCCCGGTTTTTGGCCCGGTCCCGTTTTT

GCCATCCTATTCCTACCAATGTCCGCCAAATCCTAAG        3'
CGGTAGGATAAGGATGGTTACAGGCGGTTTAGGATTCAGCT 5'
```

Synthesis of a bpFGF-encoding DNA chain is accomplished by synthesizing oligonucleotides on an applied B10 systems automatic synthesizer with overlapping complementary sequences.

The overlapping oligonucleotides are fused to form a double-stranded DNA chain, gaps being filled in with DNA polymorase and with T4 ligase. Immediately 5' of the FGF-encoding sequence in the sense strand is provided an ATG start signal, which results in an extraneous methionine being added to the N-terminus of the expressed polypeptide. Immediately 3' of the bpFGF-encoding sequence is a stop signal. At the 5' end is a Eco RI overhang and at the 3' end is a Sal I overhang, whereby the synthetic DNA strand is directly insertable in the Eco RI and Sal I site of the plasmid pUC8, described by Vieira et al. *Gene* 14, 259–268 (1982). The DNA strand is annealed into the pUC8 plasmid where it is under the control of the beta galactosidase promoter with the ATG start signal and the Shine Delgarno sequence retained in their natural orientation and association with the promoter.

The recombinant vector, designated bpFGF, is transformed into the DH-1 strain of *E. Coli* by the calcium chloride procedure, CSH, supra.

The transformed *E. Coli* is cultured in L broth, and ampicillan-resistant strains are selected. Because the DNA chain was inserted into the plasmid in an orientation which could be expected to lead to expression of protein product of the DNA chain, the ampicillan-resistant colonies are screened for reactivity with antiserum raised against bpbFGF. These colonies are screened by the immunological method of Healfman et al., *Proc. Natl. Acad. Sci. USA* 80, 31–35 (1983) in colonies reacting positively with pbFGF antibody are further characterized. The cells are separated from their culture media are lysed, and their supernatent obtained. Supernatent from transformed cells is determined by RIA to be reactive with antibody raised against bpFGF.

100 ml. of cell supernatent is obtained, and bpFGF is purified therefrom using heparin-Sepharose as described above. Approximately 0.01 mg. of FGF, purified to upwards of 98% by weight of total protein, is produced.

The biological activity of the synthetic bpFGF, which contains the extraneous N-terminal methionine residue, is tested for biological activity by the ability of the synthetic bpFGF to stimulate the proliferation of adult bovine aortic arch endothelial cells in culture, as described in *J. Cell Biol.* 97, 1677–1685 (1983). Briefly, cells (at passage 3–10) are seeded at a density of $2 \times 10^3$ cells/dish on plastic tissue culture dishes and exposed to Dulbecco's modified Eagle's medium (DMEM) supplemented with 10% calf serum. Test samples, at a dilution ranging from $10^{-1}$ to $10^{-3}$, are added on day 0 and day 2 to the dishes. On day 4, triplicate dishes are trypsinized and counted in a Coulter counter. Background levels are ordinarily $10^5$ cells/dish, while those exposed to optimal concentrations of the growth factor can contain as much as 5 to $8 \times 10^5$ cells. For a potency assay, a log response curve was established. For this purpose, 10 microliter-aliquots of a dilution (ranging from $10^{-1}$ to $10^{-5}$) of the original solution made in 0.5% bovine serum albumin (BSA)/DMEM were added in triplicate.

The biological (mitogenic) activity of synthetic bpFGF is substantially identical to natural, purified bpFGF increasing growth to at least about 5 times normal level in such 4day period, as indicated above.

The superfluous N-terminal residue is removable by partial chemical digestion with cyanogen bromide or phenyl isothiocyanate followed by treatment with a strong anhydrous acid, such as trifluoroacetic acid. However, this process attacks internal Met residues, and while providing some bpFGF having the natural protein structure, substantially reduces the total amount of biologically active protein.

EXAMPLE 3

Plasmid pbpFGF, amplified in one of the bpFGF-producing *E. Coli* clones of Example 2, is isolated and cleaved with Eco RI and Sal I. This digested plasmid is electrophoresed on an agarose gel allowing for the separation and recovery of the amplified pbFGF insert. The insert is inserted into the plasmic pYEp, a shuttle vector which can be used to transform both *E. Coli* and *Saccharomyces cerevisiae* yeast. Insertion of the synthetic DNA chain at this point assures that the DNA sequence is under the control of a promoter, in proper reading frame from an ATG signal and properly spaced relative to a cap site. The shuttle vector is used to transform URA3, a strain of *S. cerevisiae* yeast from which the oratate monophosphate decarboxylase gene is deleted.

The transformed yeast is grown in medium to attain log growth. The yeast is separated from its culture medium, and cell lysates are prepared. Pooled cell lysates are determined by RIA to be reactive with antibody raised against bpFGF, demonstrating that a peptide containing bpFGF peptide segments is expressed within the yeast cells.

The invention provides polypeptides and should make this important material available for biological and therapeutic use. The production of bpFGF can be carried out in both prokaryotic and eukaryotic cell lines. While bpFGF synthesis is easily demonstrated using either bacteria or yeast cell lines, the synthetic genes should be insertable for expression in cells of higher animals, such as mammalian tumor cells. Such mammalian cells may be grown, for example, as peritoneal tumors in host animals, and bpFGF harvested from the peritoneal fluid.

Although the above examples demonstrate that bpFGF can be synthesized through recombinant DNA techniques, the examples do not purport to have maximized bpFGF production. It is expected that subsequent selection of more efficient cloning vectors and host cell lines will increase the yield of bpFGF. Known gene amplification techniques for both eukaryotic and prokaryotic cells may be used to increase production of bpFGF. Secretion of the gene-encoded polypeptide from the host cell line into the culture medium is also considered to be an important factor in obtaining synthetic FGF in large quantities.

FGF may also be synthesized using either classical synthesis and/or solid-phase synthesis to produce peptide segments of reasonable length. Such segments can then be appropriately linked to one another to create the desired 146-residue molecule.

Brain and pituitary FGF preparations, as reported earlier, are mitogenic for a wide variety of normal diploid cultured cells derived from tissue originating from the primary or secondary mesenchyme, as well as from neuroectoderm. These include rabbit chondrocytes, bovine granulosa and adrenal cortex cells, bovine corneal endothelial cells, capillary endothelial cells derived from bovine adrenal cortex and human umbilical endothelial cells.

bpFGF peptides are useful biological materials for promoting in vitro growth of cultured cell lines, such as cell lines that have been transformed by recombinant DNA techniques to produce other useful polypeptides.

Furthermore, studies have shown that bpFGF is capable of eliciting an angiogenic response, for example, when implanted in the hamster cheek pouch or in the chick chorioallantoic membrane. Accordingly, substantially pure bpFGF peptides have potential therapeutic applications.

Substantially pure FGF polypeptides can be routinely obtained having significantly higher purity than FGF polypeptides that are extracted from mammalian tissues, such as bovine pituitaried. FGF polypeptides constitute only very minor constituents of normal mammalian tissues and thus are present only in very impure form, relative to other native polypeptides also present. Recombinant DNA techniques, for example, can be used to generate organisms or cell lines that produce the heterologous polypeptide in significantly higher proportions relative to total protein, in the cellular material and/or their secretions, than the proportions at which native FGF polypeptides are present in mammalian tissue. Because the starting material from which such synthetic FGF polypeptides are isolated has a substantially greater concentration of the heterologous polypeptide, purification techniques can fairly simply produce more highly purified FGF polypeptide fractions. Using isolation techniques such as those described in detail in the above-identified U.S. Ser. Nos. 586,518 and particularly 670,160, it is possible to routinely obtain bpFGF polypeptides which are at least about 98% pure (by weight of total proteins) and which is herein referred to as substantially pure.

Substantially pure synthetic bpFGF or the nontoxic salts thereof, combined with a pharmaceutically acceptable carrier to form a pharmaceutical composition, may be administered to mammals, including humans, either intravenously, subcutaneously, intramuscularly or orally. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed

1. Substantially pure basic fibroblast growth factor containing the amino acid sequence:

Pro—Al—Leu—Pro—Glu—Asp—Gly—Gly—Ser—Gly—
    Ala—Phe—Pro—Pro—Gly—His—Phe—Lys—Asp—Pro—
    Lys—Arg—Leu—Tyr—Cys—Lys—Asn—Gly—Gly—Phe—
    Phe—Leu—Arg—Ile—His—Pro—Asp—Gly—Arg—Val—
    Asp—Gly—Val—Arg—Glu—Lys—Ser—Asp—Pro—His—
    Ile—Lys—Leu—Gln—Leu—Gln—Ala—Glu—Glu—Arg—
    Gly—Val—Val—Ser—Ile—Lys—Gly—Val—Cys—Ala—
    Asn—Arg—Tyr—Leu—Ala—Met—Lys—Glu—Asp—Gly—
    Arg—Leu—Leu—Ala—Ser—Lys—Cys—Val—Thr—Asp—
    Glu—Cys—Phe—Phe—Phe—Glu—Arg—Leu—Glu—Ser—
    Asn—Asn—Tyr—Asn—Thr—Tyr—Arg—Ser—Arg—Lys—
    Tyr—Ser—Ser—Trp—Tyr—Val—Ala—Leu—Lys—Arg—
    Thr—Gly—Gln—Tyr—Lys—Leu—Gly—Pro—Lys—Thr—
    Gly—Pro—Gly—Gln—Lys—Ala—Ile—Leu—Phe—Leu—
        Pro—Met—Ser—Ala—Lys—Ser.

2. Basic fibroblast growth factor which is substantially pure, which is capable of stimulating proliferation of endothelial cells, and which has a MW of about 16,250, being a polypeptide containing about 140 amino acids.

3. Basic fibroblast growth factor according to claim 2 wherein the N-terminus has the sequence Pro-Ala-Leu-Pro-Glu-Asp-Gly-Gly-Ser.

4. Basic fibroblast growth factor according to claim 3 isolated from bovine pituitaries.

5. Basic fibroblast growth factor according to claim 2 isolated from bovine brain tissue.

6. Basic fibroblast growth factor according to claim 3 isolated from bovine pituitaries wherein the polypeptide has about the following amino acid composition:
Asx(12), Thr(4), Ser(9), Glx(14), Pro(9) Gly(16),Ala(9), Cys(4), Val(6), Met(2), Ile(3), Leu(13),Tyr(7),Phe(7),His(2), Trp(1),Lys(14), and Arg(12).

7. Basic fibroblast growth factor according to claim 2, which is capable of stimulating proliferation of endothelial cells in in vitro culture to at least about 5 times normal level in about 4 days.

* * * * *

UNITED STATES PATENT AND TRADEMARK OFFICE
CERTIFICATE OF CORRECTION

PATENT NO. : 4,956,455

DATED : September 11, 1990

INVENTOR(S) : Esch, et al.

Page 1 of 2

It is certified that error appears in the above-identified patent and that said Letters Patent is hereby corrected as shown below:

Column 2, line 57, after "to", insert --the--; line 58, change "a" to --at--.
Column 3, line 25, change "consituted piptides" to --constitute peptides--; line 29, change "not" to --no--.
Column 6, line 45, change "bpFRF" to --bpFGF--.
Column 7, lines 21-22, "(B) Heparin-Sepharose chromatography" should be centered as a subtitle; line 51, "Oh" should be --OH--.
Columns 9-10, the fifth pair of lines in the formula in Example 2 should read as follows:

ATGAAAGAAGATGGGCGACTACTAGCCTCCAAATGTGTAACCGAT
TACTTTCTTCTACCCGCTGATGATCGGAGGTTTACACATTGGCTA

Column 11, line 3, correct the spelling of "polymerase"; lines 22 and 25, correct the spelling of "ampicillin"; line 27, change "bpbFGF" to --bpFGF--; line 30, change "pbFGF" to --bpFGF--; line 32, after "media", insert a comma; lines 32, 33 and 35, correct the spelling of "supernatant".
Column 12, line 7, change "pbpFGF" to --bpFGF--; line 11, change "pbFGF" to --bpFGF--.
Column 13, line 10, correct "pituitaried" to "pituitaries".
Column 14, line 19, change "Al" to --Ala--.

UNITED STATES PATENT AND TRADEMARK OFFICE
CERTIFICATE OF CORRECTION

PATENT NO. : 4,956,455

DATED : September 11, 1990

INVENTOR(S) : Esch, et al

It is certified that error appears in the above-identified patent and that said Letters Patent is hereby corrected as shown below:

Column 14, line 19, change "Al" to --Ala--.

Signed and Sealed this

Fourth Day of February, 1992

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,956,455
DATED : September 11, 1990
INVENTOR(S) : Frederick S. Esch, et al It is certified that error appears in the above-indentified patent and that said Letters Patent is hereby corrected as shown below:

Column 1, as a first paragraph, insert:

This invention was made with Government support under Grants Numbers AM-18811, HD-09690, HL-20197 and EY-02186 awarded by the National Institutes of Health. The Government has certain rights in this invention.

Signed and Sealed this

Twentieth Day of December, 1994

Attest:

BRUCE LEHMAN

*Attesting Officer*  *Commissioner of Patents and Trademarks*